(12) United States Patent
Fleckenstein

(10) Patent No.: US 6,454,774 B1
(45) Date of Patent: Sep. 24, 2002

(54) DEVICE FOR INTRODUCING BRAIN PROBES

(75) Inventor: Wolfgang Fleckenstein, Mielkendorf (DE)

(73) Assignee: GMS Gesellschaft fur Medizinische Sondentechnik mbH, Mielkendorf (DE)

( * ) Notice: Subject to any disclaimer, the term of this patent is extended or adjusted under 35 U.S.C. 154(b) by 0 days.

(21) Appl. No.: 09/674,990

(22) PCT Filed: May 10, 1999

(86) PCT No.: PCT/EP99/03140
§ 371 (c)(1),
(2), (4) Date: Nov. 8, 2000

(87) PCT Pub. No.: WO99/58053
PCT Pub. Date: Nov. 18, 1999

(30) Foreign Application Priority Data

May 9, 1998 (DE) .......................... 198 20 808

(51) Int. Cl.⁷ .................................................. A61B 8/12
(52) U.S. Cl. .................... 606/108; 600/451; 600/561
(58) Field of Search ................... 600/235, 451, 600/504, 561; 606/108

(56) References Cited

U.S. PATENT DOCUMENTS

| | | | | |
|---|---|---|---|---|
| 4,206,761 A | * | 6/1980 | Cosman | 600/438 |
| 4,281,666 A | * | 8/1981 | Cosman | 600/561 |
| 4,354,506 A | * | 10/1982 | Sakaguchi et al. | 600/561 |
| 4,572,212 A | * | 2/1986 | Letterio | 600/561 |
| 4,677,985 A | * | 7/1987 | Bro et al. | 600/504 |
| 4,805,634 A | * | 2/1989 | Ullrich et al. | 600/561 |
| 4,885,002 A | * | 12/1989 | Watanabe et al. | 604/9 |
| 4,903,707 A | * | 2/1990 | Knute et al. | 600/561 |
| 4,993,425 A | * | 2/1991 | Kronberg | 600/561 |
| 5,054,497 A | * | 10/1991 | Kapp et al. | 600/561 |
| 6,080,134 A | * | 6/2000 | Lotti et al. | 604/175 |

FOREIGN PATENT DOCUMENTS

| | | |
|---|---|---|
| DE | 195 02 183 C1 | 8/1996 |
| EP | 0 617 913 A1 | 10/1994 |

OTHER PUBLICATIONS

WO 97/42870, Publication Date: Nov. 20, 1997, Expandable Parenchymal Bolt.

WO 83/03190, Publication Date: Sep. 29, 1983, Subarachnoid Bolts.

* cited by examiner

Primary Examiner—Nicholas D. Lucchesi
Assistant Examiner—Michael B. Priddy
(74) Attorney, Agent, or Firm—Rankin, Hill, Porter & Clark LLP

(57) ABSTRACT

A device for inserting a thin measurement probe into brain tissue, the device including a skull screw, a guide hose, and a compressive screw connection. The skull screw defines a longitudinal borehole through which the guide hose and a measurement probe extend. The compressive screw connection radially seals, by compression, the measurement probe and the guide hose relative to the skull screw. The guide hose serves as a protective sleeve enclosing the measurement probe and connecting the skull screw to a probe hookup. The guide hose includes further and separate lumina to receive further measurement probes and associated probe hookups, and the guide hose supports the probe hookups.

10 Claims, 2 Drawing Sheets

DEVICE FOR INTRODUCING BRAIN PROBES

BACKGROUND OF THE INVENTION

1. Field of the Invention

The invention relates to a device for insert a thin and flexible measurement probe into brain tissue.

2. Description of Related Art

Brain measuring probes are used in research and especially when intensively monitoring brain diseases or injuries, such as traumatic brain swelling associated with a skull fracture. Such measurements monitor the brain's much-reduced oxygen supply in the presence of swelling in order to allow timely surgical and medicinal intervention.

Several parameters are required in such procedures, which mutually corroborate each other and which should be ascertained as simultaneously as possible or in rapid consecutive manner. Such parameters, for instance, are the pressure inside the tissue, the partial oxygen pressure ($pO_2$), the blood flow determined by the laser doppler method, and fluorescence measurements by the NADH method of certain enzymes.

Thin and flexible brain measurement probes operating at a distal testing site are available to measure all the aforementioned parameters, and are designed to not harm the brain tissue even after being situated in the brain tissue for a substantially long time.

Appropriate devices to insert and affix the probes in the skull are already in use. They should be securely held against the skull and be tightly sealed in a sterile manner in their aperture to the brain. Such requirements are demanded especially because measurements frequently must be carried out over a period of days. The non-sterile environment and frequent patient motion must be taken into account.

A device of this kind is known from the German patent document 195 02 183 C1. The conventional skull screw used for such purposes secures strong affixation of the probes to the skull bone and sterile sealing of the skull borehole. On account of the compressive screw connection, the probe is sealed in highly sterile conditions in the screw's longitudinal borehole. The protective sleeve assures tensile load relief for the usually exceedingly traction-sensitive probes and, hence, protects them against damage caused by patient movements. However, this known design incurs the drawback that the probes can only be used one at a time. Moreover, this design inherently is appropriate only for $pO_2$ probes. Other parameters would have to be determined from separately-situated probes entailing additional skull drillings.

A more appropriate design of this kind is known from KATALOG 93/94 issued by GESELLSCHAFT FUER MEDIZINISCHE SONDENTECHNIK GMB, Dorfstrasse 2, D-24247 Kiel-Mielkendorf and from INTRACRANIAL INSERTION SYSTEM, IIS 3-way system. The skull screw disclosed therein comprises three mutually adjacent accesses to its longitudinal borehole. These accesses allow installing simultaneously the probes each with its own compressive screw connection. Accordingly three parameters may be determined simultaneously.

Unfortunately, this design requires laborious handling. Three compressive screw connections must be operated separately with ensuing heightened risk of leakage and hence loss of sterility at one of the connections. The screw being used requires special and expensive manufacture. Each probe requires separate traction relief. High costs are thus incurred by the hospital because of conventional single use of the probes. Also, there is a substantial drawback in that the probes enter the brain at different angles through the longitudinal borehole and, inside the brain, run in a mutually-diverging manner. If, in the event of operational error, the skull screw is rotated with its probes in place, the brain tissue shall be stirred with exceedingly disadvantageous consequences for the patient.

A design different from the above-discussed species is known from SCHAEDELBEFESTIGUNG [skull affixation] PF 190, drawing of Mar. 25, 1994, Perimed AB, Järfälla, Sweden which was made public by distribution from the exhibition stand of GMS GESELLSCHAFT FUER MEDIZINISCHE SONDENTECHNIK MBH at the $45^{th}$ annual exhibition of the German Society of Neurosurgery at Nuremberg, 19 through May 25, 1994.

The above known insertion device consists of a resilient stopper fitted with several boreholes to pass probes. The stopper is inserted into the skull borehole and can be compressed in the longitudinal direction using a screwdriver. As a result the skull borehole as well as the probes passing through the stopper are sealed.

However, this design entails the drawback first of the unreliable, resilient support against the skull bone. Furthermore both the sealing between the stopper and the skull borehole as well as the sealing of the probes inside the stopper are highly unreliable.

This design, therefore, can be put in place only by means of a cumbersome and extensive operation whereby, following insertion, the stopper and its outward directed lines run subcutaneously.

This known design offers the advantage of allowing simultaneous emplacement of several probes while suffering from the drawback of being impractical for routine use in a neuro-surgical intensive care facility.

SUMMARY OF THE INVENTION

An objective of the present invention is to create a device of the above species which is more economical, simpler and installed in more reliable manner.

In this design of the invention, several probes can be installed through several lumina of the same guide hose. This feature offers economy. A conventional, simple skull bone screw with one compressive screw connection is required. The guide hose at the same is a traction relief means for the probes and furthermore renders the manufacture more economical. The skull bone screw being used assures reliable fastening at the skull bone and good sealing and sterility of the skull borehole. By means of the known compressive screw connection, the probes are sealed in highly sterile manner inside the guide hose. Accordingly excellent sterility is assured. Since the compressive screw connection requires only driving a screw, installation and handling are simplified by the invention. Lastly, this invention offers the advantage that the probes run parallel in the lumina of the guide hose and into the brain tissue. In case of accidental rotation of the skull screw or of the protective tube, therefore, there will be only slight tissue damage in the brain. On the whole, the design of the invention is substantially more economical, simpler and more reliable than the known designs.

In further accordance with the present invention, the highly pressure-sensitive probes are protected by the protective sleeve in the area where they cross the very hard meninx.

All probe connections may be situated in mutually juxtaposed manner at the proximal, external end of the protective sleeve. However, in further accordance with the present invention, the probe connections can be implemented at the ends of the branched tubes individually and without being hampered by the other connections. Using flexible branched tubes, the probe evacuation means can be configured into different directions to corresponding hook-up elements.

In accordance with other features, the invention provides the advantage—relative to the equally applicable design of a separate sealing ring—of greater economy and easier handling because the sealing ring need not be handled separately. Moreover. the invention provides defined length adjustment of the protective sleeve.

In accordance with other features of the invention, because the applicable materials are few on account of tissue compatibility, sterilization properties and the like concerning the guide hose, the plastically deforming sealing ring tends to flow deformation due to the compression. This compression can be maintained long-term by a resilient element such as a rubber ring.

Provided there are correspondingly standardized length adjustments for the individual probes, these probes can be configured in very simple manner at the desired depths of insertion without the complexity of adjustment. When designing the guide hose in the manner of claim 3, the branch tubes for instance can be made into appropriate lengths.

As already cited above, the material selection of the guide hose is restricted by the various requirements for the tube. Appropriate materials are mostly low in resiliency. When compressing the guide hose in order to reliably seal in this manner the probes in the compression zone, the guide hose material must be compressed within the compression zone. This requirement is met also with respect to the other requirements on suitable materials. However, problems arise when dissolving the compressed connection if, in the case of insufficient restoring force, the guide hose no longer detaches off the probes and these probes then cannot be pulled. In such an event the entire guide hose together with all probes must be removed and inserted again. The present invention is designed to minimize or eliminate these problems. The guide hose in the zone of compressed sealing is made of another material of high resiliency and, in particular, offers a high restoring force. In this way reliable compressed sealing of the probes is assured under all circumstances and following disengagement of the compressed connection the probes shall be detached completely and therefore can be easily exchanged individually. The remaining elements of the guide hose—namely its two segments, one proximally and one distally from the compressible part—may be better matched during material selection to the desired requirements regardless of their resiliencies, that is for instance relative to tissue compatibility, good sterilization, tensile strength etc.

The compressible part also may be compressed externally in known manner using a resilient compression ring. Advantageously, however, and in accordance with the present invention, the compressive screw connection axially compresses the flange and in this manner mechanically upsets the compressible part in the axial direction, as a result of which it implements the required probes' radial, compressive sealing. Consequently, a very simple and reliable design has been attained.

The compressible part may be connected, for instance by bonding or welding or suitable mechanical interlocking, at the adjoining ends of the proximal and distal ends of the guide hose into one assembled unit. However, such connections can be implemented on plastics only with difficulty and in particular tissue compatibility most of the time precludes bonding by adhesives. In this respect, further features of the invention are advantageous. By a fully separate design of the compressible part, the problems are circumvented and construction is simplified.

A guide hose fitted with a wholly separate compressible part can be installed only with difficulty in the device of the invention because the guide hose—which consists of a distal segment, a proximal segment and the compressible part—would have to be held by three hands during assembly. In this respect, the present invention is advantageous and provides an easily handled assembly unit of all three segments of the guide hose wherein the securing pin, for instance, is a mandril or guide wire installed in the one of the lumina, or also a special securing pin situated only between the ends of the proximal and distal segments of the guide hose that adjoin the compressible part.

BRIEF DESCRIPTION OF THE DRAWINGS

These and further features of the invention will be apparent with reference to the following description and drawings, wherein.

DETAILED DESCRIPTION OF THE PREFERRED EMBODIMENTS

Figure 1:
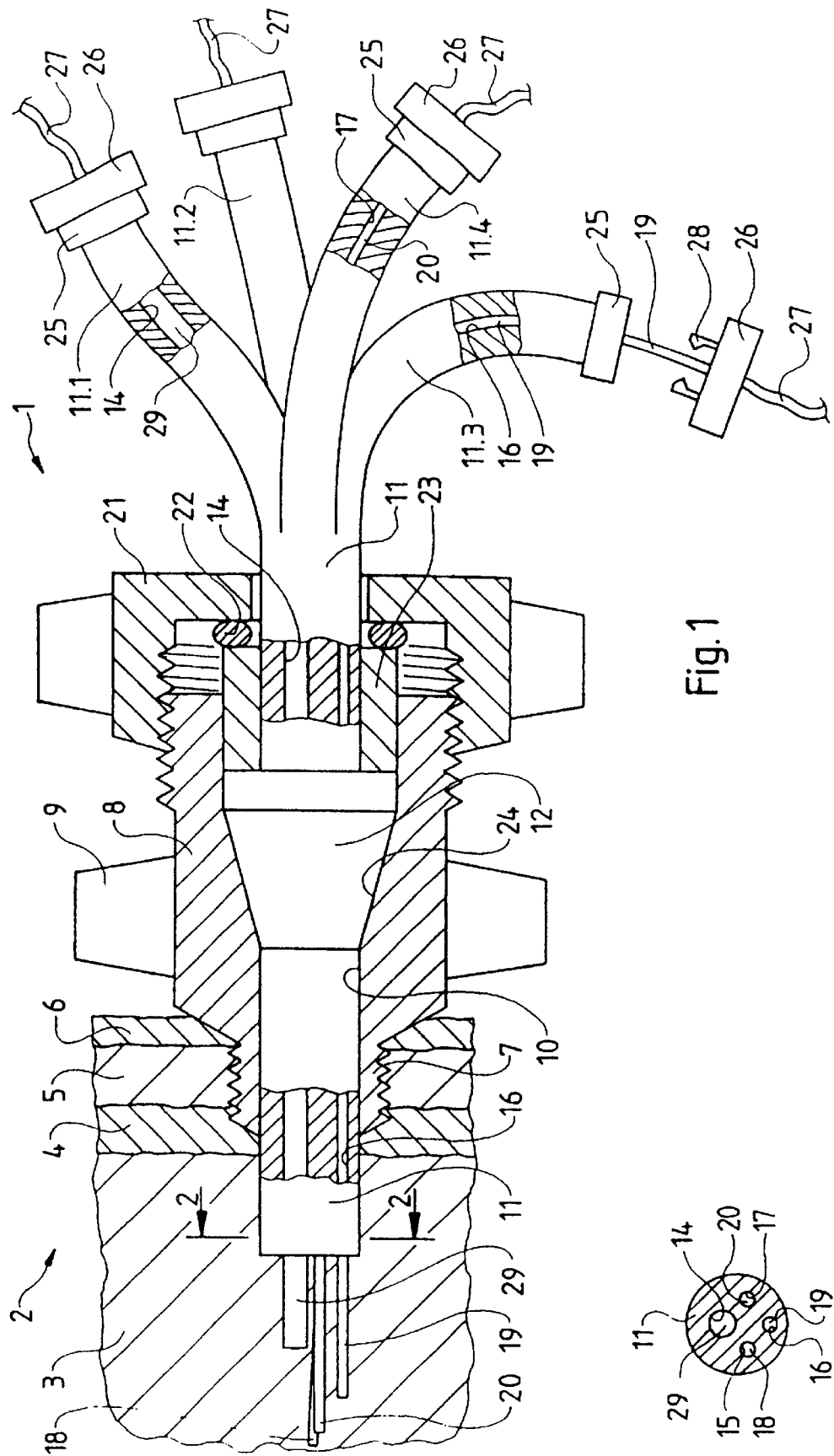
FIG. 1 is a longitudinal section of the device of the invention.

FIG. 1 shows an insertion device 1 in the installation position at a patient's skull 2, and shows a section of the brain tissue 3, the meninx 4, the skull bone 5 and the scalp 6.

The distal thread 7 of a skull screw 8 is threaded into a previously implemented skull borehole passing through the skull bone 5 while the scalp 6 is sealed off by corresponding conical surfaces of the skull screw: Skull-screw wings 9 assist in the in the insertion-threading procedure.

A guide hose 11 runs inside a longitudinal borehole 10 passing through the skull screw 8 and, at a defined site along its length, is fitted with an integral sealing ring 12 which, in this embodiment, is conical.

Figure 2:
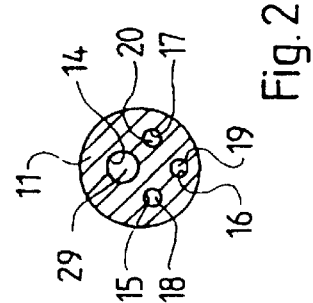
FIG. 2 is a section along line 2—2 of FIG. 1.

The guide hose 11 (also see FIG. 2) is solid and made of an appropriate. pliant material fitted with several, in this instance four, longitudinal ducts, that hereafter are called the "lumen/lumina".

The lumina are used to pass long, resilient measurement probes and may be of different inside diameters. A larger lumen 14 passes a thicker measurement probe 29 whereas three narrower lumina 15, 16 and 17 pass three thinner measurement probes 18, 19 and 20.

The skull screw 8 is fitted at the proximal end of the longitudinal borehole 10 with a compressive screw connection constituted by a compression nut 21. The nut 21 is screwed by its inside thread onto the proximal end of the skull screw 8 and by means of a resilient, for instance rubber ring 22 loading a displaceable sleeve 23 resting against the end face of the conical sealing ring 12 which in turn is compressed against an inner cone 24 of the skull screw 8.

Upon tightening the compression nut 21, the sealing ring 12 is compressed against the inner cone 24 such that it deforms radially inward while compressing the measurement probes 18, 19 and 20 in their particular lumina 15, 16 and 17 to thereby seal the lumina while simultaneously sealing the guide hose 11 relative to the skull screw 8. Care must be taken that, to assure reliable compression, the installed measurement probes be fitted with outside diameters that shall match the inside diameters of the particular lumina. Where no probe is required in a lumen, a filling rod must be provided at least in the zone of the compressive seal.

Proximally outside the skull screw 8, the guide hose 11 of this embodiment branches off into several branch tubes 11.1, 11.2, 11.3 and 11.4. Each lumen of the guide hose 11 continues into one of the branch tubes, for instance the lumen 14 into the branch tube 11.1 and the lumen 17 into the branch tube 11.4.

A probe hookup is configured at each proximal end of each branch tube 11.1 through 11.4 and consists each time of a connector element 25 at the side of the branch tube and a connector element 26 at the side of the probe. The probe-side connector element 26 is fitted distally with one of the measurement probes 29, 18, 19 or 20 and proximally with a line 27 leading to a test apparatus (not shown). Line 27, depending on the kind of probe used, may be an electric, optic or hydraulic signal transmission line.

The connector element 25 and 26 are shown apart with respect to the branch tube 11.3. The measurement probe 19, accordingly, has been pulled some distance out of the guide hose 11. In this illustrative embodiment, a pair of clamps 28 allows connecting the two connector elements 25 and 26 in snap-in manner.

In an omitted embodiment mode, the guide hose 11 also may run free of branching to its proximal end where the hookups of the various probes, for instance, may be situated at a common connector.

The branch tubes 11.1 through 11.4 may be of different lengths. They may match in length the particular probes to be inserted in such a way that the measurement probes shall project into the brain at different discrete depths. In this manner the distal measurement sites probes can be configured in desired manner.

Because the sealing ring 12 is integral with the guide hose 11 and hence situated at a defined length on the guide hose, then the guide hose—following implementation of the compressive connection by the skull screw 8 into its affixation position in the skull bone 5—shall be kept in place at a defined length relative to the brain. As a result the desired depth position of the measurement probes will be assured.

As shown in FIG. 1 and on condition that the end segment of the guide hose 11 situated distally from the sealing ring 12 be of commensurate length, the guide hose 11 shall pass through the scalp 4 and reliably protect the measurement probes sensitive at that site against the strong forces applied by the scalp 4.

Figure 3:
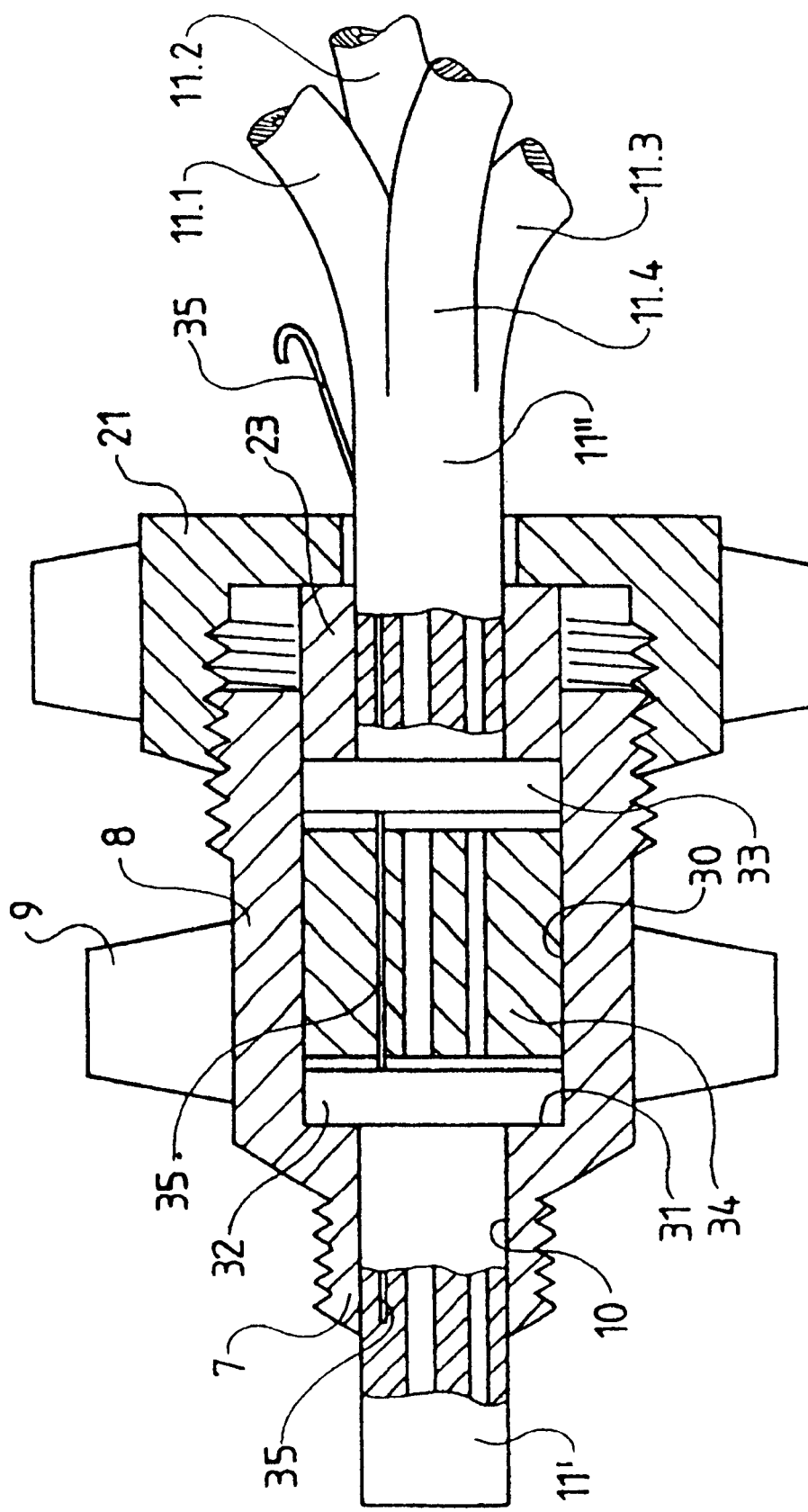
FIG. 3 is a section corresponding to FIG. 2 of an embodiment variation of the device fitted with a compressible part.

FIG. 3 shows an embodiment variation of the design of FIG. 1. Whenever possible the same references are used. The patient skull 2 shown in FIG. 1 and the probes 18, 19, 20 and 29 have been omitted for the sake of graphical clarity.

The skull screw 8 and the compressive nut 21 as well as the displaceable sleeve 23 correspond to the design of FIG. 1. The resilient ring 22 of FIG. 1 is omitted because it is not required in this design. Immediately proximally adjoining the skull screw 8, a borehole 30 replacing the inner cone 24 is present in the longitudinal borehole of the skull screw 8 and is engaged by the displaceable sleeve 23. The borehole 30 is bounded by its step 31 by the longitudinal borehole 10.

While the guide hose 11 is integral in the embodiment of FIG. 1, it is divided in the embodiment of FIG. 3 into a distal segment 11' and a proximal segment 11". The proximal end of the distal segment 11' comprises an external flange 32 and the distal end of the proximal segment 11" comprises an external flange 33. The two external flanges 32 and 33 are integral with the segments 11' and 11" of the guide hose and fit by their outside diameters into the borehole 30. When the compressive screw connection is implemented (i.e., when tightening the compressive screw 21 against the skull screw 8) the two external flanges 32 and 33 therefore are displaced toward each other.

A compressible part 34 is mounted between the two external flanges 32 and 33 and, as shown by FIG. 3, is separate from the guide-tube segments 11' and 11". The compressible part 34 consists of another material than the guide-tube segments. More specifically, the compressible part 34 is made of a highly resilient material exhibiting an especially high restoring force.

The outside diameter of the compressible part 34 corresponds to the inside diameter of the borehole 30 and, as shown, comprises the same ducts, that is lumina 14, 15, 16 and 17 as the guide-segment segments 11' and 11" which are the same in the embodiment of FIG. 3 as in that of FIG. 1.

The compression nut 21 can be tightened once the guide segment segments 11' and 11" and the compressible part 34 are configured in the manner shown in FIG. 3, and once the probes are inserted in the manner shown in FIG. 1. As a result the external flanges 32 and 33 are displaced axially toward each other and come to rest in compressing manner against the axial ends of the compressible part 34 which they axially compress. Externally the compressible part 34 comes to rest against the borehole 30 and thereby compresses inward the probes inserted into its lumina while constituting a highly sterile seal.

After the compressive screw connection has been disengaged, the highly resilient and well restoring compressible part 34 returns into its initial shape while repelling the proximal guide hose segment 11" and widening its lumina and hence wholly freeing the probes inside the lumina. The probes may then be easily removed and for instance exchanged.

In order to assure the mutual configuration shown in FIG. 3 of the two guide-tube segments 11' and 11" and the compressible part 34, the external flange 32, 33 and the compressible part must be concentric and the lumina must be aligned. A securing pin 35 is provided that runs axially parallel in the guide hose segments 11' and 11" and in the compressible part 34. In this embodiment mode the pin is affixed, illustratively by welding, in the segment 11'. However, the pin is supported in a longitudinally displaceable manner in the compressible part 34 and in the guide hose segment 11". This pin 35 proximally projects from the guide hose segment 11" as shown in FIG. 3 and, at that site, is bent into a hook. The securing pin 35 secures the three guide hose segments to each other while nevertheless allowing them to be displaced axially in order to set up and dissolve the compression connection.

The securing pin 35 may be omitted in another embodiment mode. Securing the guide hose segments and the compressible part may be useful when assembling the guide hose and may be implemented using guide wires that pass through guide-tube lumina instead of the probes. Alternatively, the compressible part 34 also may be firmly joined to the guide hose segments 11' and 11" for instance by bonding or welding the end faces or by implementing a secure connection by appropriately mechanically interlocking these end faces.

What is claimed is:

1. A device to insert a thin and flexible measurement probe into brain tissue comprising:

a skull screw;

a guide hose defining a lumen receiving a measurement probe, said lumen having a proximal end, said guide hose and said measurement probe being received within a longitudinal borehole in said skull screw;

said device further comprising a compressive screw connection to radially seal in a compressive manner the measurement probe and the guide hose at the skull screw, and wherein said guide hose acts as a protective sleeve enclosing the measurement probe and connecting the skull screw to a probe hookup; and, wherein said guide hose defines additional lumina, each additional lumina having a proximal lumina end and a probe hookup supported at said proximal lumina end, said additional lumina being adapted to receive additional measurement probes.

2. The device as claimed in claim 1, wherein the guide hose has a distal end and a proximal end, said guide hose including a defined compression site at a location between said distal end and said proximal end, and wherein a distal section of said guide hose extends between said compression site and said guide hose distal end and has a length such that, when installed, the guide hose passes through a scalp and toward the brain tissue.

3. The device as claimed in claim 1, wherein the guide hose has a proximal section extending from said skull screw and wherein, when installed, the guide hose proximal section branches off into a plurality of branches, each of said plurality of branches defining one of said additional lumina.

4. The device as claimed in claim 1, wherein lengths of the measurement probes and lengths of the lumina are matched to each other so that a depth of installation of distal ends of the measurement probes differ from one another.

5. The device as claimed in claim 1, further comprising a plastically deformable sealing ring enclosing the guide hose, said sealing ring being integral with the guide hose.

6. The device as claimed in claim 5, wherein the compressive screw connection comprises a prestressable spring element.

7. The device as claimed in claim 1, wherein the guide hose includes a distal hose segment and a proximal hose segment that are connected to one another by a compressive sealing segment, said distal hose segment and said proximal hose segment being made from a first material, and wherein said compressive sealing segment is formed from a compressible part that is made from a second material, said second material having a higher elasticity and restoring force than said first material.

8. The device as claimed in claim 7, wherein ends of the distal and proximal guide hose segments adjoining the compressible part are fitted with integral, external flanges to axially compress the screw connection.

9. The device as claimed in claim 8, wherein the compressible part is separate from the distal and proximal segments of the guide hose.

10. The device as claimed in claim 9, wherein a securing pin connects the distal and proximal segments of the guide hose, said securing pin passing through the compressible part.

* * * * *

UNITED STATES PATENT AND TRADEMARK OFFICE
CERTIFICATE OF CORRECTION

PATENT NO. : 6,454,774 B1
DATED : September 24, 2002
INVENTOR(S) : Fleckenstein

It is certified that error appears in the above-identified patent and that said Letters Patent is hereby corrected as shown below:

Column 2,
Line 26, after "unreliable", do not begin new paragraph.
Line 50, delete "scaled" and insert -- sealed --.

Column 3,
Line 11, after "Moreover" delete "." (period) and insert -- , -- (comma).

Signed and Sealed this

Eleventh Day of February, 2003

JAMES E. ROGAN
*Director of the United States Patent and Trademark Office*